(12) United States Patent
Lion

(10) Patent No.: US 8,545,902 B2
(45) Date of Patent: Oct. 1, 2013

(54) DOSAGE FORMS OF PLANT-DERIVED CATHARTICS

(75) Inventor: Nicholas Lion, Las Vegas, NV (US)

(73) Assignee: Nicholas Lion, Las Vegas, NV (US)

( * ) Notice: Subject to any disclaimer, the term of this patent is extended or adjusted under 35 U.S.C. 154(b) by 0 days.

(21) Appl. No.: 13/326,571

(22) Filed: Dec. 15, 2011

(65) Prior Publication Data

US 2012/0156143 A1 Jun. 21, 2012

Related U.S. Application Data

(60) Provisional application No. 61/459,572, filed on Dec. 15, 2010.

(51) Int. Cl.
*A01N 65/00* (2009.01)

(52) U.S. Cl.
USPC .......................................... 424/725

(58) Field of Classification Search
None
See application file for complete search history.

(56) References Cited

U.S. PATENT DOCUMENTS

| | | |
|---|---|---|
| 471,879 A | 3/1892 | Myers |
| 5,498,425 A | 3/1996 | Wood et al. |
| 5,514,663 A | 5/1996 | Mandel |
| 5,674,522 A | 10/1997 | Shah et al. |
| 6,083,531 A | 7/2000 | Humbert-Droz et al. |
| 6,121,215 A | 9/2000 | Rau |
| 6,444,198 B1 | 9/2002 | Daggy et al. |
| 6,461,638 B1 | 10/2002 | Note-Simonnard |
| 6,589,551 B1 | 7/2003 | Jolliffe |
| 6,645,528 B1 | 11/2003 | Straub et al. |
| 6,764,696 B2 | 7/2004 | Pather et al. |
| 6,866,873 B2 | 3/2005 | Stern |
| 7,247,324 B1 | 7/2007 | Wehling et al. |
| 2006/0039973 A1 | 2/2006 | Aldritt et al. |
| 2010/0215758 A1 | 8/2010 | Opheim |
| 2012/0156143 A1 | 6/2012 | Lion |

OTHER PUBLICATIONS

Balsari, A., et al., "The fecal microbial population in the irritable bowel syndrome", Microbiologica, 1982, 185-94, vol. 5 No. 3 (Abstract only).

Bradley, P.R., "British Herbal Compendium", 1992, 52-4, vol. 1, British Herbal Medicine Association, Bournemouth, England. (Book, not included).

Brinker, F., et al., "Herb Contraindications and Drug Interactions", 1998, 69-70, Eclectic Medical Publication, Sandy OR. (Book, not included).

Elmer, G.W., "Probiotics: Living Drugs", Am. J. Health-Syst. Pharm., Jun. 15, 2001, 1101-1109, vol. 58 No. 12.

Favier, C., et al., "Fecal beta-D-galactosidase production and *Bifidobacteria* are decreased in Crohn's disease", Dig. Dis. Sci., 1997, 817-822, vol. 42 No. 4.

Gibson, G.R., et. al., "Regulatory effects of bifidobacteria on the growth of other colonic bacteria", J. Appl. Bacteriol., 1994, 412-420, vol. 77.

Kailasapathy, K. Microencapsulation of probiotic bacteria: technology and potential applications, 2002, Curr. Issues Intest. Microbiol. 3: 39-48.

Lee, R.E., "Effervescent Tablets: Key Facts About a Unique, Effective Dosage Form", Tablets and Capsules, Jul. 2004, 1-4.

Newall, et al., "Herbal Medicines: A Guide for Health Care Professionals", 1996, 243-244, The Pharmaceutical Press, London, England. (Book, not included).

Petticrew, M., et al., "Systematic Review of the Effectivenes of Laxatives in the Elderly", Health Technol. Assess, 1997, 1-52, vol. 1 No. 13.

Saavendra, J.M., et al., "Feeding of *Bifidobacterium bifium* and *Streptococcus thermophilus* to infants in hospital for prevention of diarrhoea and shedding of rotavirus", Lancet, Oct. 15, 1994, 1046-9, vol. 344.

Van Der Wiel-Korstanje, J.A.A., et al., "The faecal floral in ulcerative colitis", J. Med. Microbiol., 1975, 491-501, vol. 8 No. 4.

*Primary Examiner* — Michael Meller
(74) *Attorney, Agent, or Firm* — Potter Anderson and Corroon LLP

(57) ABSTRACT

Compositions for improved delivery of plant-derived cathartics are disclosed. In one aspect, the compositions comprise a plant-derived cathartic and an effervescence coupling system that, when dissolved into an aqueous medium such as water, produce an effervescent liquid cathartic composition. In another aspect, the compositions comprise a solid dosage form that dissolves or disperses in an aqueous medium to produce a liquid composition that is administered to an individual. The liquid compositions are not only more appealing to a consumer, but also improve the amount and bioavailability of active cathartic components. The cathartic composition is administered to an individual alone or in combination with one or more agents that promote additional laxation, digestion or gastrointestinal health, and/or improve the effectiveness of the plant-derived cathartic composition.

8 Claims, No Drawings

DOSAGE FORMS OF PLANT-DERIVED CATHARTICS

Benefit is claimed under 35 U.S.C. §119(e)(1) of the filing date of U.S. Provisional Application No. 61/459,572, filed Dec. 15, 2010, the entire contents of which are incorporated by reference herein.

FIELD OF THE INVENTION

The present invention is in the field of cathartics. In particular, the invention provides novel oral dosage formulations of plant-derived laxatives, which improve palatability and bioavailability of active components.

BACKGROUND OF THE INVENTION

Senna is a common term that typically refers to dried leaflets of the plant *Cassia senna* L. (synonym: *C. angustifolia* Vahl, *C. angustifolia* Delile, and *C. acutifolia* Defile). Upon ingestion, very little of the senna active substances are systemically absorbed by the body. Senna contains anthraquinones, including diathrone glycosides, sennosides A and B (rhein diathrones), sennosides C and D (rhein aloe emodin heterodianthrones), and other minor sennoside compounds, which all seem to contribute to a laxative effect in humans. Sermosides A and B are of particular utility in creating a laxative effect and have been used in the production of medicinal cathartic preparations. Senna contains hydroxyanthracene glycosides that are not fully absorbed in the upper gastrointestinal tract are converted into active aglycones by mircoflora in the large intestine and additional bacterial enzymes in the colon, which stimulates colonic motility and affects fluid and electrolyte balance in the colon.

Similarly, anthraglycosides found in alder buckthorn (*Frangula alnus*, synonym: *Rhamnus frangula*) and cascara products (*Frangula pershiana*, synonym: *Rhamnus persiana*) have cathartic properties; such examples to name few are Cascara sagrada, buckthorn bark, bitter bark, chittem bark, yellow bark, dogwood bark, *Rhamni pershianae* Cortex, and sagrada bark. Cascara sagrada contains cascarosides A and B (anthraglycosides), which are responsible for increased peristalsis in the large intestine. Cathartic preparations of Cascara sagrada extracts are standardized to contain 25% to 30% hydroxyanthracene derivatives per dose. Casanthranol A and B (anthranol glycosides) derived from Cascara sagrada are used in cathartic preparations. Casanthranol A and B upon oxidative hydrolysis yield more active anthraquinone aglycones and glycosides, i.e., cascarosides A (emodin) and B (aglycone) forms of anthraglycosides.

The use of senna and other plant-derived cathartics dates back to about the 9th century A.D. when physicians medicinally employed senna, for example, as a cathartic; the leaves were brewed into a tea and the tea was administered to patients for its strong laxative effect. Today, senna and other plant species are still typically administered as aqueous infusions. For example, an herbal tea of Chinese mallow senna leaf (*Cassia angustifolia*), is prepared by steeping the leaves in hot water. Several disadvantages of such teas are (1) its unpleasant taste and appearance, and (2) the inconvenient and extended time (up to 20 minutes) needed for the preparation of the tea before it is steeped sufficiently, of efficacious strength, cooled sufficiently, and then ready to drink.

Problems with laxatives include their overall effectiveness as well as the unpredictable amount of time from ingestion to laxative action for the user. Delivering a useful active stimulant laxative product to various sections of the gastrointestinal tract in high enough concentration to have clinical effect is desirable, yet overdosing and localized high concentrations of active laxative product can yield adverse cramping effects in the upper gastrointestinal tract (duodenum and jejunum), when strong peristalsis is desired globally in the lower gastrointestinal tract, i.e. the ileum and colon. Therefore, poorly prepared delivery of solid oral dosage systems of herbal laxatives (e.g., encapsulated senna leaf powder) and OTC laxative drugs (e.g., poorly dissolving tablets) have their shortcomings in efficacy to affect motility of the ileum and colon in part because of pharmacodynamic delivery.

For instance, various encapsulated senna leaf powders count on the body's gastrointestinal tract to "steep the tea" into solution in vivo where the stomach is a highly acidic pH environment. This leads to slow solubility of active laxative compounds and may lead to localized high concentrations where the Senna leaf powder may settle in contact with the lumen of the gastrointestinal tract versus global lumen surface contact. Drinking a senna tea would be more efficacious than ingesting an encapsulates senna leaf powder but on the other hand is much less convenient than a capsule, and the taste is unpleasant.

The formulation of plant-derived laxatives in effervescent compositions has not been described previously, though effervescent compositions and processes are known. For example U.S. Pat. No. 7,247,324 B1 describes methods for delivering guava extract using effervescent formulations; US Patent application 2010/0215758 A1 describes effervescent formulations for the delivery of polyunsaturated fatty acids; U.S. Pat. No. 6,764,696 B2 pertains to the effervescent formulations of drugs, to increase the bioavailability of drugs in different parts of the gastrointestinal tract including esophagus, duodenum and colon; US 2006/0039973 A1 provides an effervescent composition for the delivery of dietary fiber; U.S. Pat. No. 5,498,425 describes a phosphosoda buffered saline laxative containing pineapple flavoring; U.S. Pat. No. 5,514,663 pertains to laxative enteric coated compositions of sennosides with the express purpose of releasing the sennosides substantially near the junction between the small intestine and the colon or within the colon; U.S. Pat. No. 6,083,531 describes effervescent formulations that disintegrate rapidly, within 15 seconds, in the mouth to deliver pain medications and other drugs.

Another notable problem with conventional delivery of plant-derived laxatives and other medically valuable plant derivatives is the solubility and the presence, concentration, and location of the biologically active plant derivatives. For example, hydroxyanthracene glycosides that are not fully absorbed in the upper gastrointestinal tract are converted into active aglycones by mircoflora in the large intestine. Another problem is the overuse of antibiotics, wherein the gastrointestinal tract loses symbiotic commensal microorganisms that produce catalytic enzymes. Such enzymes help activate plant-derived cathartic compound and derivatives into biologically active laxative derivatives. Administering probiotic and enzyme products can facilitate the effectiveness of plant-derived cathartics and their derivative compounds.

The following references are believed to describe the state of the art concerning (a) *Cassia senna*, (b) Cascara (*Rhamnus persiana*), including Cascara sagrada and buckthorn bark, (c) *Lactobacillus* bacteria (genus) including *L. acidophilus*, and (d) Bifidobacteria (28 species) including *B. bifidum* (bifidus), *B. lactis*, and B. spp: Brinker F., Herb Contraindications and Drug Interactions, Sandy O R: Eclectic Medical Publication, 1998, 70; Newall C A, Anderson L A, and Phillipson J D, Herbal Medicines: A Guide for Health Care Professionals, London, England: The Pharmaceutical Press, 1996, 243-4;

Bradley P R, ed, British Herbal Compendium, Vol. 1, Bournemouth, England: British Herbal Medicine Association, 1992, 52-4; Petticrew M, Watt I, and Sheldon T, "Systematic Review of the Effectiveness of Laxatives in the Elderly," Health Technol Assess, 1997, 1(13): i-iv, 1-52; Balsari A, Ceccarelli A, Dubini F, et al, Microbiologica, 1982, 5(3): 185-94; Elmer G W, Am J Health Syst Pharm, 2001, 58(12): 1101-9; Favier C, Neut C, Mizon C, et al, Dig Dis Sci, 1997, 42(4):817-22; Gibson G R and Wang X, J Appl Bacteriol, 1994, 77(4):412-20; Saaverdra J M, Bauman N A, Oung I, et al, "Lancet, 1994, 344(8929):1046-9; and Van der Wiel-Korstanje J A and Winkler K C, J Med Microiol, 1975, 8(4): 491-501.

In view of the discussion set forth above, it is clear that a need exists for an improved dosage form of plant-derived cathartics.

SUMMARY OF THE INVENTION

The present invention is directed to a convenient ready-made solid formulation ready for rapid in situ conversion to an effervescent drink that comprises a plant-derived cathartic/laxative such as a senna or cascara product, its extract or its constituent compounds (e.g., sennosides or cascarosides and their derivatives). This solid to effervescent liquid conversion is unique and novel for this application because it has been surprisingly found that senna compounds, sennosides for example, develop increased solubility during the effervescent process. In other words, it has been unexpectedly found that the plant laxative compounds, the effervescence coupling system, and/or the process used to produce effervescence, substantially increase the solubility of plant-derived cathartic compounds, such as sennosides and other plant-derived glucosides, thus increasing the dosage form efficiency, potency, and the overall effectiveness and user appeal of the plant-derived laxative effervescent dosage formulation. Furthermore, the application and method of employing probiotic microorganisms, e.g. *Bifidobacterum* and *Lactobacillus* bacteria and/or the manufactured and isolated enzymes from such microorganisms that convert plant-derived cathartic laxative compounds to more biologically active derivatives, both before and after the agents are consumed, to enhance the availability of biologically active plant cathartic laxative derivatives from the effervescent plant cathartic product system. The combined probiotic microorganism system, enzyme system, and the effervescent cathartic laxative system synergistically facilitate more bioavailability of active plant cathartic derivatives in an accelerated fashion to the user clinically than otherwise. Furthermore, dissolved cathartics laxatives, probiotics, and enzymes in a voluminous solution provides a liquid medium that facilitates accelerated synergies among those constituents, and such liquid medium also serves as a vehicle to deliver those clinically active compounds targeting a greater clinical surface area of the gastrointestinal lumen, than otherwise by non-liquid oral dosage forms.

One aspect of the invention features a composition comprising one or more plant-derived cathartics and an effervescence coupling system. In various embodiments, the cathartic is obtained from senna (*Cassia senna*); canafistula (*Cassia fistula*); common buckthorn (*Rhamnus cathartica*), alder buckthorn (*Rhamnus frangula*), cascara buckthorn (*Rhamnus persiana*); fo-ti (*Polygonum multiflorum*); or damiana (*Turnera diffusa*), or combinations of those plants. The plant-derived cathartic can provided as fresh or dried plants or plant parts. Alternatively or additionally, the plant-derived cathartic is provided as an extract of plants or plant parts. The extract can be standardized for one or more cathartic compounds.

In some embodiments, the plant-derived cathartic is a cathartic compound, or mixture of cathartic compounds, or derivative of a cathartic compound, or an isomer of a cathartic compound, or a purified isolate of a cathartic compound. In certain embodiments, the compound is selected from anthraquinone glycosides (anthraglycosides), anthraquinone derivatives, anthraglycoside derivatives, cascarosides, casanthrols, hydroxyanthracene, hydroxyanthracene derivatives, hydroxyanthracene glucosides, hydroxyanthracene aglycones, sennosides, naturally-occurring senna compounds, chemically modified naturally occurring senna compounds, purified isolates thereof, and any combination thereof.

In one embodiment, the pharmaceutically suitable effervescence coupling system of the composition comprises an acid-base coupling system. The base can be a carbonate or bicarbonate, among others. The acid can be citric acid, fumaric acid, adipic acid, malic acid, tartaric acid, salts thereof or combinations thereof.

In one embodiment, the composition is prepared as a solid dosage form. The solid forms can be tablets, granules or powders. In one embodiment, the solid dosage form dissolves or disperses in an aqueous medium to form a liquid composition prior to administration to an individual. In a particular embodiment, the solid dosage form dissolves or disperses in an aqueous medium within about five minutes at room temperature. The solid dosage form may further comprise one or more of: (a) encapsulated matrices, (b) coated formats, (c) mixtures with food products, and (d) mixtures with beverage products.

In various embodiments, the cathartic compositions of the invention comprise one or more additional ingredients selected from flavors, fragrances, sweeteners, colorings, defoaming surfactants, and combinations thereof. In particular embodiments, (a) the flavors or fragrances include apple, sour apple, raspberry, watermelon, pomegranate, lemon, lime, orange and combinations thereof; (b) the sweeteners include fructose, sucrose, mannitol, sorbitol, stevia, aspartame, saccharin and combinations thereof; (c) the colorings include riboflavin, cobalamin and combinations thereof; and (d) the defoaming surfactants include docusate sodium salt, docusate potassium salt, docusate calcium salt and combinations thereof.

In various embodiments, the cathartic compositions of the invention comprise one or more additional ingredients selected from probiotic microorganisms, enzymes, stool softeners, osmotic laxatives, magnesium hydroxide; soluble and insoluble dietary fiber, antiflatulents, antibloating agents, nutraceuticals, B vitamins, brewers yeast, and combinations thereof. In particular embodiments, (a) the stool softeners include docusate sodium, docusate potassium, docusate calcium and combinations thereof; (b) the osmotic laxatives include magnesium citrate, polyethylene glycol, magnesium hydroxide and combinations thereof; (c) the dietary fiber includes gum, pectin, mucilage, psyllium and combinations thereof; (d) the antiflatulents/antibloating agents include simethicone, fennel, ginger and combinations thereof; and (e) the nutraceuticals include *Panax quinquefolius* (ginseng), *Zingiber officinale* (ginger), *Echinacea angustifolia* (Echinacea), *Uncaria guianensis* (Cat's Claw), *Rosa canina* (Rose Hips), *Foeniculum vulgare* (Fennel), *Berberis vulgaris* (Barberry), *Phyllanthus emblica* (Gooseberry), *Castanea sativa* (Chestnut) and combinations thereof.

In certain embodiments, the probiotic microorganisms, or the enzymes, or both, increase the amount or improve the in vitro and/or in vivo availability of active cathartic compounds, or facilitate conversion of less active to more active forms of cathartic compounds in the composition upon dissolution or dispersion of the composition in an aqueous medium to form the liquid composition. In one embodiment, some or all of the microorganisms, or the enzymes, or both, are formulated for pre-determined release upon dissolution into the aqueous medium, before and/or after ingestion.

The probiotic microorganisms can be members of genera selected from *Bacillus, Bifidobacterium, Enterococcus, Lactobacillus, Lactococcus, Saccharomyces, Streptococcus*, and combinations thereof. More particularly, the probiotic microorganisms can be species selected from *Bacillus subtilis, Bifidobacterium adolescentis, Bifidobacterium bifidum, Bifidobacterium animalis, Bifidobacterium thermophilum, Bifidobacterium breve, Bifidobacterium longum, Bifidobacterium pseudolongum, Bifidobacterium infantis, Bifidobacterium lactis, Enterococcus faecium, Lactobacillus acidophilus, Lactobacillus brevis, Lactobacillus bulgaricus, Lactobacillus casei, Lactobacillus cellobiosus, Lactobacillus crispatus, Lactobacillus curvatus, Lactobacillus delbrueckii, Lactobacillus fermentum, Lactobacillus GG (Lactobacillus rhamnosus* or *Lactobacillus casei* subspecies *rhamnosus*), *Lactobacillus gasseri, Lactobacillus johnsonii, Lactobacillus paracasei, Lactobacillus plantarum, Lactobacillus reuteri, Lactobacillus salivarus, Lactococcus lactis, Lactococcus plantarum, Saccharomyces boulardii (cerevisiae), Streptococcus faecium, Streptococcus thermophilus, Streptococcus salivarus*, and combinations thereof.

The enzymes can be selected from amylase, protease, lipase, trypsin, papain, bromelain, lysozyme, chymotrypsin, esterases, carboxylesterases, acetylcholinesterase, butyrylcholinesterase, paraoxonase, and arylesterase, pancreatic enzymes, liver enzymes, and combinations thereof, among others.

Another aspect of the invention features a solid composition comprising one or more plant-derived cathartics, formulated to dissolve or disperse in an aqueous medium to form a liquid composition prior to administration to an individual. In one embodiment, the solid composition is formulated to dissolve or disperse in an aqueous medium within a few minutes, such as about five minutes, of exposure to the medium at room temperature.

In one embodiment, the solid composition further comprises at least one probiotic microorganism, at least one enzyme, or a combination thereof. In certain embodiments, the probiotic microorganisms, or the enzymes, or both, increase the amount or improve the in vitro and/or in vivo availability of active cathartic compounds, or facilitate conversion of less active to more active forms of cathartic compounds in the composition upon dissolution of the composition in the aqueous medium to form the liquid composition. In certain embodiments, some or all of the microorganisms, or the enzymes, or both, are formulated for pre-determined release upon dissolution into the aqueous medium and/or after ingestion into the gastrointestinal tract.

The probiotic microorganisms can be members of genera selected from *Bacillus, Bifidobacterium, Enterococcus, Lactobacillus, Lactococcus, Saccharomyces, Streptococcus*, and combinations thereof. More particularly, the probiotic microorganisms can be species selected from *Bacillus subtilis, Bifidobacterium adolescentis, Bifidobacterium bifidum, Bifidobacterium animalis, Bifidobacterium thermophilum, Bifidobacterium breve, Bifidobacterium longum, Bifidobacterium pseudolongum, Bifidobacterium infantis, Bifidobacterium lactis, Enterococcus faecium, Lactobacillus acidophilus, Lactobacillus brevis, Lactobacillus bulgaricus, Lactobacillus casei, Lactobacillus cellobiosus, Lactobacillus crispatus, Lactobacillus curvatus, Lactobacillus delbrueckii, Lactobacillus fermentum, Lactobacillus GG (Lactobacillus rhamnosus* or *Lactobacillus casei* subspecies *rhamnosus*), *Lactobacillus gasseri, Lactobacillus johnsonii, Lactobacillus paracasei, Lactobacillus plantarum, Lactobacillus reuteri, Lactobacillus salivarus, Lactococcus lactis, Lactococcus plantarum, Saccharomyces boulardii (cerevisiae), Streptococcus faecium, Streptococcus thermophilus, Streptococcus salivarus*, and combinations thereof.

The enzymes can be selected from amylase, protease, lipase, trypsin, papain, bromelain, lysozyme, chymotrypsin, esterases, carboxylesterases, acetylcholinesterase, butyrylcholinesterase, paraoxonase, and arylesterase, pancreatic enzymes, liver enzymes, and combinations thereof, among others.

Another aspect of the invention features a method to enhance the clinical performance of (1) a composition comprising a plant-derived cathartic and an effervescence coupling system or (2) solid composition comprising one or more plant-derived cathartics, formulated to dissolve in an aqueous medium to form a liquid composition. The method comprises administering the composition to an individual in conjunction with probiotic microorganisms, or with enzymes, or with both, wherein the microorganisms and/or enzymes increase the amount or improve the availability of active cathartic compounds, or facilitate conversion of less active to more active forms of cathartic compounds in the composition upon dissolution of the composition in the aqueous medium to form the liquid composition, thereby enhancing the clinical performance of the composition.

In one embodiment, the method comprises incorporating the microorganisms and/or enzymes into the plant-derived cathartic composition, mixing the composition with an aqueous medium to form the liquid composition, and administering the liquid composition to the individual. In another embodiment, the method comprises formulating the microorganisms and/or enzymes separately from the plant-derived cathartic composition, mixing the cathartic composition and the separately formulated microorganisms and/or enzymes with an aqueous medium to form a liquid composition, and administering the liquid composition to the individual.

In certain embodiments, the probiotic microorganisms are of genera selected from *Bacillus, Bifidobacterium, Enterococcus, Lactobacillus, Lactococcus, Saccharomyces, Streptococcus*, and combinations thereof, and may be selected from the species listed above. In certain embodiments, the enzymes are selected from amylase, protease, lipase, trypsin, papain, bromelain, lysozyme, chymotrypsin, esterases, carboxylesterases, acetylcholinesterase, butyrylcholinesterase, paraoxonase, and arylesterase, pancreatic enzymes, liver enzymes, and combinations thereof.

In certain embodiments, some or all of the microorganisms, or the enzymes, or both, are formulated for pre-determined release upon dissolution into the aqueous medium, before and/or after ingestion by the individual. In one embodiment, the clinical performance of the composition is improved by increasing conversion of anthraquinones, hydroxyanthracene glycosides, and anthraglycosides into more active cathartic forms. In particular, conversion of hydroxyanthracene glycosides to hydroxyanthracene aglycones is increased.

Another aspect of the invention features a method of administering a plant-derived cathartic to an individual. The method comprises (1) formulating the plant-derived cathartic into a solid dosage form that dissolves or disperses in an aqueous medium; (2) dissolving or dispersing the a dosage form into the aqueous medium, thereby producing a liquid composition comprising the plant-derived cathartic, and (3) administering the liquid composition to the individual. In one embodiment, the solid dosage form comprises an effervescence coupling system and the liquid composition formed thereby is effervescent.

In one embodiment, the liquid composition is administered immediately following completion of dissolution or dispersion of the solid dosage form. In another embodiment, liquid composition is administered minutes to hours following completion of dissolution or dispersion of the solid dosage form.

One embodiment of the method comprises administering the plant-derived cathartic in conjunction with probiotic microorganisms, or with enzymes, or with both. These agents are selected for their ability to increase the amount or improve the in vitro and/or in vivo availability of active cathartic compounds, or facilitate conversion of less active to more active forms of cathartic compounds in the composition upon dissolution of the composition in the aqueous medium to form a liquid composition.

One embodiment comprises incorporating the microorganisms and/or enzymes into the plant-derived cathartic composition, mixing the composition with an aqueous medium to form a liquid composition, and administering the liquid composition to the individual. Another embodiment comprises formulating the microorganisms and/or enzymes separately from the plant-derived cathartic composition, mixing the cathartic composition and the separately formulated microorganisms and/or enzymes with an aqueous medium to form a liquid composition, and administering the liquid composition to the individual.

The probiotic microorganisms or enzymes, or both, can be administered before, together with, or after administering the plant-derived cathartic composition. One embodiment comprises supplying one or more of the cathartic composition, the probiotic microorganisms and the enzymes as components of a kit, wherein the kit comprises instructions for administration of the kit components. In certain embodiments, some or all of the microorganisms, or the enzymes, or both, are formulated for pre-determined release upon dissolution into the aqueous medium and/or after ingestion by the individual.

The probiotic microorganisms can be of genera selected from *Bacillus, Bifidobacterium, Enterococcus, Lactobacillus, Lactococcus, Saccharomyces, Streptococcus*, and combinations thereof. In particular, they can be selected from the bacterial species listed above. The enzymes can be selected from amylase, protease, lipase, trypsin, papain, bromelain, lysozyme, chymotrypsin, esterases, carboxylesterases, acetylcholinesterase, butyrylcholinesterase, paraoxonase, and arylesterase, pancreatic enzymes, liver enzymes, and combinations thereof, among others.

Another aspect of the invention features a kit comprising, in separate containers in a single package or in separate containers in a virtual package: (a) one or more plant-derived cathartic-containing solid dosage form that dissolves or disperses in an aqueous medium at room temperature within minutes of exposure thereto and produces a liquid cathartic composition that is optionally effervescent; and (b) instructions for how to use the kit components for the benefit of an individual. The kit may further comprise one or more of: (1) one or more probiotic microorganisms that promote digestion or gastrointestinal health, or enhance the effectiveness of the cathartic composition; and (2) one or more enzymes that promote digestion or gastrointestinal health, or enhance the effectiveness of the cathartic composition. In one embodiment, the kit comprises the plant-derived cathartic-containing composition and other optional components, and instructions for administration per rectum.

Another aspect of the invention features a package comprising (1) a plant-derived cathartic-containing solid dosage form that, upon dissolution in an aqueous medium, produces a liquid, cathartic composition that is optionally effervescent; and (2) a label affixed to the package containing a word or words, picture, design, symbol, acronym, slogan, phrase, or other device, or combination thereof, that indicates that the contents of the package contains a composition suitable for promoting laxation in an individual. In one embodiment, the package includes a solid dosage form that fits into a standard size of bottled drinking water and its container assembly, optionally comprising instructions for using commercially available bottled drinking water to dissolve the solid dosage form and, optionally, instructions for consuming the liquid composition immediately to over an extended period. In another embodiment, the package includes a solid dosage form kit assembly system integrated into a bottled drinking water container.

Another aspect of the invention features an article of manufacture for communicating information about or instructions for use of a plant-derived cathartic-containing solid dosage form that, upon dissolution in an aqueous medium, produces a liquid, optionally effervescent, cathartic composition, alone or with other beneficial agents, wherein the article of manufacture comprises one or more of a physical or electronic document, digital storage media, optical storage media, audio presentation, audiovisual display, or visual display containing the information or instructions. In one embodiment, the article of manufacture includes instructions for using commercially available bottled drinking water to dissolve the solid dosage form and, optionally, instructions for consuming the liquid composition immediately to over an extended period.

Another aspect of the invention features a method of manufacturing a solid dosage form comprising plant-derived cathartics and an optional effervescence coupling system. The method comprises combining active and inactive ingredients and forming them into a solid dosage form for dissolution or dispersion into an aqueous medium to produce a liquid dosage form.

Other features and advantages of the invention will be apparent from the detailed description and examples that follow.

DETAILED DESCRIPTION OF ILLUSTRATIVE EMBODIMENTS

Definitions

The terms "cathartic," "laxative," "emetic" and/or "purgative" are used interchangeably herein to describe a composition (e.g., food, dietary supplement, nutraceutical or pharmaceutical agent) that stimulates or otherwise promotes emptying of the bowels.

A "plant-derived cathartic" as used herein refers to a cathartic, laxative, emetic or purgative whose active agents are contained within plant tissue or obtained from plant tissue. Thus, a "plant-derived cathartic" includes, for example, fresh, dried, crushed, powdered or otherwise prepared whole plants or plant parts, such as leaves, stems, flowers, seeds, roots and/or bark of a plant containing active laxative agents, as described herein. A "plant-derived cathartic" also includes active and ancillary compounds purified, separated, isolated, or otherwise obtained from a whole plant or plant part, as described in greater detail herein. Furthermore, "plant-derived cathartic" active agents are commercially available from botanical extract suppliers and fine chemical suppliers.

As used herein, an "extract" of a plant containing cathartic agents, e.g., a "senna extract" refers to a material produced by extraction of one or more substances from plant material into a solvent. Suitable solvents depend on the nature of the substances desired to be extracted, and are well known in the art of plant-derived cathartics. They can include water or water miscible organic solvents, such as alcohols (for example, ethanol), or acids and bases, or nonpolar solvents such as pentane, hexane, or heptanes, to name a few. Extracted materials are typically evaporated to dryness and can be stored as such, or resuspended in a suitable medium. The term "standardized extract" as used herein refers to an extract containing a known amount of one or more substances extracted from the plant. For instance, a senna extract may be standardized to contain 10% by weight total sennosides.

A "product" of a plant containing cathartic agents, e.g., a "senna product" refers to the whole plant, or parts of the plant in whole, crushed, ground or powdered form.

A "compound" of a plant containing cathartic agents, e.g., a "senna compound" refers to the active laxative components of the plant, e.g., sennosides from the senna plant. The term is intended to be used inclusively, and can refer to a single cathartic compound, or mixture of cathartic compounds, or a derivative of a cathartic compound, or an isomer of a cathartic compound, or a purified isolate of a cathartic compound, for example.

The term "cathartic-containing plant" or "CCP" refers collectively to all plants that contain cathartic or laxative agents as described herein.

"Effervescence" is understood in the art as the reaction (in an aqueous medium, such as water) of certain acids and bases to produce carbon dioxide. Typical acids used in this reaction include but are not limited to citric, malic, tartaric, adipic, and fumaric acid. Typical bases used in the effervescent reaction include but are not limited to sodium bicarbonate, potassium bicarbonate, sodium carbonate, and potassium carbonate. As used herein, the term "effervescence coupling system" refers to the acid and base components that are combined to produce carbon dioxide, bicarbonate ions, and fizzing mechanical agitation.

The terms "pharmaceutically suitable," "pharmaceutically acceptable, "biologically acceptable, "biologically compatible," "physiologically acceptable" and the like are used interchangeably herein to refer to coupling systems, carriers, excipients, media, esters, salts, cations or anions, and the like that are well known in the art as being suitable for use in preparing the dosage forms described herein and administering such dosage forms to an individual.

The terms "individual," "subject," "patient," "person," and the like are used interchangeably herein to refer to an individual animal of any species or kind, including a human unless a non-human animal is specified.

The term "effective amount" means an amount of a compound, material, composition, dietary supplement, medicament, or other material that is effective to achieve a particular biological result, such as a laxative or cathartic effect.

The term "in conjunction with" means that a drug, supplement, food, or other substance is administered to an individual (1) together, e.g., in a composition, or (2) separately, e.g., at the same or different time, and/or the same or different frequency, using the same or different administration routes. When administration is "separate" the drug, supplement, food, or other substance can be also given about the same time or periodically. "About the same time" generally means that the substances are administered at the same time or within about 72 hours of each other. "Periodically" means that the substance is administered on a dosage schedule acceptable for a specific substance.

The term "in vitro" as used herein refers to the chemical and biological actions, interactions and reactions that occur upon dissolution of a solid dosage form of plant-derived cathartic into an aqueous liquid medium to form a liquid dosage form. The term "in vivo" refers to the chemical and biological actions, interactions and reactions that occur following ingestion of the liquid dosage form into the body of an individual.

As used herein, the term "oral administration" or "orally administering" means that an individual ingests one or more of the substances described herein. The term "ingestion" is used herein interchangeably with the term "oral administration."

The term "single package" means that the components of a kit are physically associated in or with one or more containers and considered a unit for manufacture, distribution, sale, or use. Containers include, but are not limited to, bags, boxes, bottles, shrink wrap packages, stapled or otherwise affixed components, or combinations thereof. A single package may be containers of individual food compositions physically associated such that they are considered a unit for manufacture, distribution, sale, or use.

The term "virtual package" means that the components of a kit are associated by directions on one or more physical or virtual kit components instructing the user how to obtain the other components, e.g., in a bag containing one component and directions instructing the user to go to a website, contact a recorded message, view a visual message, or contact an instructor to obtain instructions on how to use the kit.

All percentages expressed herein are by weight of the composition on a dry matter (or "dry weight") basis unless specifically stated otherwise. The skilled artisan will appreciate that the terms "dry matter basis" or "dry weight basis" mean that the amount of the ingredient present in the composition is expressed relative to the composition after the free moisture in the composition is removed.

Dosages expressed herein are generally indicated as milligrams or grams (mg or g), or as milligrams or grams per kilogram of body weight (mg/kg or g/kg) unless expressed otherwise.

As used herein, ranges are used herein in shorthand, to avoid having to list and describe each and every value within the range. Any appropriate value within a given range can be selected, where appropriate, as the upper value, lower value, or the terminus of the range.

As used herein, the singular form of a word includes the plural, and vice versa, unless the context clearly dictates otherwise. Thus, the references "a", "an", and "the" are generally inclusive of the plurals of the respective terms. For example, reference to "a compound" or "a method" includes a plurality of such "compounds" or "methods." Similarly, the words "comprise", "comprises", and "comprising" are to be interpreted inclusively rather than exclusively. Likewise the terms "include", "including" and "or" should all be construed to be inclusive, unless such a construction is clearly prohibited from the context.

The terms "comprising" or "including" are intended to include embodiments encompassed by the terms "consisting essentially of" and "consisting of". Similarly, the term "consisting essentially of" is intended to include embodiments encompassed by the term "consisting of".

The term "and/or" is a shorthand term for the alternative and the inclusive. Accordingly, the term "and/or" as used herein means one or the other, or one and the other.

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

Description

The present invention springs in part from the inventor's discovery of several benefits arising from the formulation of cathartic-containing plant products, extracts or compounds with an effervescence coupling system to produce a novel effervescent dosage form upon dissolution in an aqueous medium, such as water. In an illustrative example, two standardized stock samples of senna extract (a 20% w/w and a 10% w/w according to suppliers' specifications) and a preparation comprising an effervescence coupling system were analyzed in an independent laboratory using high pressure liquid chromatography (HPLC). The total sennosides measured in the stock samples varied significantly: the standardized 20% w/w stock (200 mg) showed a low yield result of 163.6 mg and the standardized 10% w/w stock (100 mg) also reported a low yield of 55.3 mg, that is a 36.4 mg and 44.7 mg difference respectively from the claimed concentration values of the stock suppliers. By comparison, the effervescent formulation containing senna extract, which was made using the same standardized 10% w/w stock sample, yielded a 103% total sennosides.

It is noteworthy that, to prepare the senna extracts for HPLC, the extracts were made miscible in an aqueous medium using ultrasonic mixing and 30% w/w organic solvents in water. Such efforts were not needed for the extract combined with the effervescence coupling system, where the process used to produce effervescence outperformed standard laboratory assay preparation techniques. Indeed, the solid tablet dosage form had a superior dissolution time of less than four minutes and a superior solubility as demonstrated in the HPLC assay tests yielding a 103%. Thus, the effervescent mechanism(s) and a plant-derived cathartic create a novel and advantageous delivery system heretofore unexploited for such types of plants and active components.

Without intending to be bound by any particular explanation of the mechanisms underlying the present invention, it is believed that the effervescent dosage form facilitates bioavailability of plant cathartic active components in at least two ways. First, the effervescent medium is believed to render the active components more chemically available by promoting conversion of less active components to their more active counterparts, e.g., through solubilization and isomerization facilitated by interaction with ions formed in the effervescent solution. A second mechanism believed to contribute to the availability of laxative components from the novel formulation of the invention is kinetic agitation, i.e., "fizzing and bubbling" of the effervescent reaction to rapidly and completely liberate and dissolve the active compounds. Another mechanism, related more to the solid-to-liquid dosage transition is that the liquid volume can accelerate interaction among system components, and such liquid volumes can reach more clinically relevant surface areas of the gastrointestinal tract or otherwise. To illustrate these principles as they pertain to senna, sennoside B has the same solubility characteristics as sennoside A, but B is more soluble and can be recrystallized from large amounts of hot water. Sennoside A can be slowly isomerized to B in a bicarbonate solution, such as would be used as a part of an effervescence coupling system. This supports why herbal tea preparations, ancient or modern, are effective. Hot water and time lead to more sennosides dissolved into liquid and more isomerized sennoside A to sennoside B (a medicinally desirable active sennoside). This isomerization of sennoside A to B in bicarbonate is also a positive factor for the novel formulation of the present invention. Overall, the effervescence mechanism creates an enhanced condition for the molecular isomerization, generation of bicarbonate ions, greater solubility, and kinetic agitation that positively effect plant derived plant cathartic compounds to be ingested orally and introduced into the gastrointestinal tract to render desired clinical laxative activity.

To illustrate further, during the same independent lab testing of senna samples as described above, one commercially available senna tea bag ("Cali Girl brand Dieters' Drink") was steeped in 180 milliliters of boiled water for eight minutes to determine the total sennosides dissolved into solution. The process yielded approximately 150 milligrams of total sennosides per tea bag. By comparison, senna extract formulated into an effervescent formulation of the invention was also determined to deliver up to 150 milligrams of total sennosides dissolved into 180 milliliters of water completely forming a colored but clear aqueous solution at ambient room temperatures. Thus, the traditionally medicinal senna brewed tea preparations can now be had in a ready-made enhanced effervescent solid form that is nearly instantly ready to use upon dissolution into water in less than four minutes with improved taste, aroma, and visual appearance in color are enhanced characteristics over the traditional pale bitter brewed senna tea.

Thus, one aspect of the invention features a composition comprising a plant-derived cathartic and an effervescence coupling system. The plant-derived cathartic can be selected from one or more, or any combination of, plants or plant parts containing cathartic/laxative components, sometimes referred to collectively herein as "cathartic-containing plants" ("CCPs"). The plant-derived cathartics may include plant products, plant extracts or plant compounds as have been defined herein. Any plant that contains a cathartic/laxative component is suitable for use in the present invention. For instance, suitable plants include, but are not limited to: senna (*Cassia senna* L., synonym *C. angustifolia, C. acutifolia*); canafistula (*Cassia fistula*); various buckthorns, including but not limited to common buckthorn (*Rhamnus cathartica*), alder buckthorn (*Frangula alnus*, syn. *Rhamnus frangula*, cascara buckthorn (cascara, also known as Cascara Sagrada (sacred bark), chittam, chittem or chitticum bark, bitter bark, dogwood bark and yellow bark) (*Rhamnus persiana* syn *Rhamnus pershiana* syn *Frangula pershiana*); fo-ti (*Polygonum multiflorum*); and damiana (*Turnera diffusa*). As used herein "Cascara Sagrada" refers to the bark of the cascara buckthorn and preparations thereof.

As mentioned, CCPs may be used as whole or fresh plants or plant parts, or they may be dried, ground, powdered, or prepared as extracts in accordance with known methods. In certain embodiments, standardized extracts are prepared or obtained from commercial sources. For example, a pharmaceutically suitable senna extract standardized to contain 10% or 20% total sennosides is commercially available (Blue California, Rancho Santa Margarita Calif. 92688).

Cathartic/laxative compounds may also be utilized in addition to or instead of the plant products or extracts described above. Suitable plant-derived compounds include but are not limited to anthraquinone glycosides, anthraquinone derivatives, sennosides (such as A, B, C, D, E, or F) and other naturally occurring or chemically modified senna anthraglycosides, anthraglycoside derivatives, cascarosides (such as A & B), casanthranols (such as A & B), hydroxyanthracene glucosides, hydroxyanthracene aglycones and hydroxyanthracene derivatives, to name a few. Pharmaceutically suitable isolated and purified cathartic compounds can be prepared by known methods or obtained from commercial sources (e.g., Spectrum Chemicals and Laboratory Products, New Brunswick, N.J. 08901).

More particularly, senna contains several sennosides, which act to stimulate peristalsis of the small and large intestine. Cascara Sagrada contains cascarosides A and B (anthraglycosides), which are responsible for increased peristalsis in the large intestine. Cathartic preparations of Cascara Sagrada extracts are standardized to contain 25% to 30% hydroxyanthracene derivatives per dose. Casanthranol A and B (anthranol glycosides) derived from Cascara Sagrada are used in cathartic preparations. Casanthranol A and B upon oxidative hydrolysis yield more active anthraquinone aglycones and glycosides, i.e., cascarosides A (emodin) and B (aglycone) forms of anthraglycosides.

Plant products, extracts and/or compounds can be interchangeable or combinable to achieve a particular effect. For example, senna extract could be substituted with a correlated amount of purified mixed sennosides. The same can be said of Cascara Sagrada and its related derivatives, cascarosides (mixtures of A and B) or casanthranols (mixtures of A and B) or its purified B form, or similarly a pure sennoside (such as sennoside B). The skilled artisan will understand that the employment of different plant-derived cathartic sources, including and not limited to, senna, Cascara Sagrada, Fo-ti, buckthorn, and damiana, and their mixtures thereof, can be used in given effervescent formulations, applications, and methods of the invention.

The effervescence coupling system can be any suitable acid/base pair, or combination of acids and bases, that will yield carbon dioxide when combined in an aqueous medium, such as water. Nonlimiting examples of suitable bases include bicarbonates, such as sodium or potassium bicarbonate ($NaHCO_3$, $KHCO_3$), and carbonates, such as sodium, potassium or calcium carbonate ($Na_2CO_3$, $K_2CO_3$ $CaCO3$). Nonlimiting examples of suitable acids include citric acid, fumaric acid, adipic acid, malic acid and tartaric acid.

The plant-derived cathartic(s) and the effervescence coupling system are combined into solid dosage forms, such as tablets, granules or powders, in accordance with established methods. Furthermore, the plant-derived cathartic(s) and the effervescent coupling system combination can be modified and adapted for per rectum administration, in accordance with established methods, as an alternative route of introduction into the gastrointestinal tract. Depending on the dosage form, additional components may be needed or desired; for instance, typical pharmaceutical carriers, excipients, salts and the like, binders such as dextrose, sorbitol, xyitol or lactose, lubricants such as sodium benzoate, polyethylene glycol or adipic acid, preservatives, lubricants, oils, colorants, fragrances and flavorants, including sweeteners and artificial or natural flavors. In addition, a defoaming surfactant, such as docusate sodium (sodium sulfosuccinate), added to the formulation can facilitate a smooth and pleasant appearance of the "fizzing" effect by breaking the surface tension of the aqueous medium as the solid effervescent dissolves into solution and $CO_2$ gas is evolved and released during the effervescent chemical reaction. Docusate sodium is approved for use in food and has been used in carbonated and non-carbonated beverages as a wetting agent or solubilizer for flavor emulsion stabilizers. Docusate sodium present in very small amounts (e.g., 1 mg) is an approved food additive and offers no laxative consequences. As a therapeutic adjunct to the present invention, docusate sodium or docusate calcium can also serve as a concomitant active laxative ingredient when present in therapeutically high concentrations (e.g., 100 mg) to act clinically as a stool softener.

The dosage form can contain a range of pre-determined dosages in accordance with known effective ranges, with the understanding that one benefit of the present invention is that a larger amount of the active components will be available due to the novel mode of delivery. Typically, the compositions of the invention will be formulated to deliver at least 1 mg of active components per dose. In particular embodiments, the compositions are formulated to contain at least 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg per dose. Appropriate dosages for different individuals are known in the art in many cases. For instance, the FDA recommends 100 mg sennosides per day for adults, 50 mg per day for children 6-12 years of age and 25 mg per day for children 2-6 years of age, in divided doses (e.g., 50 mg, 25 mg, or 12.5 mg twice daily for adults, children 6-12 or children 2-6, respectively).

Thus, in one embodiment, the effervescent preparation contains standardized senna extract (10% w/w sennosides), $NaHCO_3$, citric acid, flavors, fragrance, colors and sweeteners. This effervescent application of a plant-derived cathartic laxative improves the solubility and bioavailability of active laxative senna compounds and other active derivatives by the nature and process of the effervescent mechanism creating a clear colored senna containing liquid that is medicinally effective, a convenient, and more pleasing to the consumer to drink.

In another embodiment, 250 mg of a standardized senna extract (10% w/w) in the above formulation is replaced with 125 mg senna extract (20% w/w). Both formulations deliver 25 mg of sennosides, but the 20% formulation has a 125 mg total weight reduction in overall dosage weight, which allows for additional ingredients to be added, such as more flavorings.

In another embodiment, the senna extract (10% w/w) in the above formulation is replaced with purified sennosides, such as a mixture of sennosides A & B or sennoside B.

In another embodiment, the senna extract (10% w/w) in the above formulation is reduced by a fraction and Cascara sagrada is added to form a cathartic mixture of plant-derived laxative ingredients. Other cascara products may also be utilized in a mixture, such as buckthorn bark. Furthermore, active ingredient "extracts" may have their corresponding active derivatives substituted in their place; for example, the cascara product "extracts" may employ purified cascarosides and casanthranols.

In another embodiment the effervescence coupling system may employ other acid-base components where the $NaHCO_3$ base component may be substituted with and not limited to $KHCO_3$ and $CaCO_3$ and their mixtures.

In another embodiment, the effervescence coupling system may employ other acid-base components where the citric acid component may be substituted with and not limited to fumaric acid, tartaric acid, malic acid, adipic acid and the salts thereof, and their mixtures.

In other embodiments, the flavors, fragrance, colors, and defoaming surfactants composition may employ: apple (flavor and fragrance), sour apple, raspberry, watermelon, pomegranate, lemon, lime, orange, mannitol, sorbitol; fructose (sweeteners), sucrose, stevia, aspartame, saccharin; riboflavin (color), B12; docusate sodium salt (defoaming surfactant), docusate potassium salt, docusate calcium salt; and constituents in continuation and not limited to, respectively, and their mixtures, may be utilized.

In other embodiments, additional beneficial components can be added to the cathartic compositions. These include, but are not limited to: stool softeners such as docusate sodium, potassium or calcium as mentioned elsewhere herein; osmotic laxatives such as magnesium citrate or polyethylene glycol; magnesium hydroxide; probiotic microflora as described in detail below; soluble dietary fiber such as pectin, insoluble dietary fiber such as psyllium; antiflatulents/antibloating agents such as simethicone, fennel or ginger, nutraceuticals such as *Panax quinquefolius* (ginseng), *Zingiber officinale* (ginger), *Echinacea angustifolia* (Echinacea), *Uncaria guianensis* (Cat's Claw), *Rosa canina* (Rose Hips), *Foeniculum vulgare* (Fennel), *Berberis vulgaris* (Barberry), *Phyllanthus emblica* (Gooseberry), *Castanea sativa* (Chestnut); certain enzymes as described in detail below; B vitamins and brewers yeast.

In another embodiment, the senna extract (10% w/w) in the above formulation is replaced with ground raw senna leaflet product, but which may be considered less pleasant and convenient and may require straining or filtering before the oral effervescent drink is ingested by mouth.

In another embodiment, the senna extract (10% w/w) in the above formulation is replaced with a mixture ground raw senna leaflet product, senna extract and sennosides compounds.

Senna and senna-like plant products contain anthraquinones and hydroxyantrthracene glycosides that are not fully absorbed in the upper intestinal tract, but they are converted into active aglycones by the microorganisms in the large intestine and additional bacterial enzymes in the colon. Sennosides are effectively prodrugs, which effectively are not absorbed in the upper gastrointestinal tract but are activated by bacterial enzymes in the lower gastrointestinal tract. Senna and its clinically active constituent compounds and enzymatically activated derivatives stimulate colon motility and affects fluid and electrolyte balance in the colon. Moreover, other senna-like plant sources containing anthraquinone derivatives which exert a stimulant laxative effect, include and are not limited to, Fo-ti (*Polygonum multiflorum*, also known as knotweed) and damiana (*Turnera diffusa*).

Cascara (*Frangula pershiana*, also known as *Rhamnus persiana*) products and cascara-like plant products (e.g., alder buckthorn) contain anthraglycosides. Furthermore, the anthraglycosides in Cascara sagrada, cascarosides A and B (like that to senna and sennosides A and B), also increase peristalsis of the intestines. Cascara products have very little effect on the small intestine but exerts effects on the large intestine; microorganisms of the lower gastrointestinal tract convert anthraglycosides into active stimulant laxatives causing peristalsis and bowel evacuation.

In addition to the Senna and Cascara products, other plant-derived cathartic laxative products may also comprise a given formulation composition, and mixtures thereof, that are in the spirit of the invention. Thus, any plant-derived cathartic, its constituents, and constituent derivatives that contain useful anthraquinones, hydroxyantrthracene glycosides, anthraglycosides, and their cathartically active derivatives, are useful in a given effervescent formulation compositions of the invention.

A distinct improvement to the action of anthraquinones, hydroxyantrthracene glycosides, anthraglycosides, and their cathartically active derivatives are enhancements by the integrated formulation system where probiotic flora are incorporated into a given effervescent plant-derived cathartic formulation. Probiotic microorganisms and other microorganisms provide synergistic improvement for the cathartic activity induced by anthraquinones, hydroxyantrthracene glycosides, and anthraglycosides, and their cathartically active derivatives that are from plant sources.

Accordingly, in other aspects of the invention, the effervescent plant cathartic/laxative formulation includes other active or beneficial ingredients. In one embodiment, probiotic mircoflora are incorporated into the composition or administered in conjunction with the composition. Such organisms are known in the art; beneficial genera include but are not limited to: *Streptococcus, Enterococcus, Lactobacillus, Lactococcus, Bacillus, Bifidobacterium*, and *Saccharomyces. Enterococcus* species include, without limitation, various probiotic strains of *Enterococcus faecium. Streptococcus* species include, without limitation, *Streptococcus faecium, Streptococcus thermophilus*, and *Streptococcus salivarus. Lactobacillus* species include, without limitation, *Lactobacillus acidophilus, Lactobacillus brevis, Lactobacillus bulgaricus, Lactobacillus casei, Lactobacillus cellobiosus, Lactobacillus crispatus, Lactobacillus curvatus, Lactobacillus delbrueckii, Lactobacillus fermentum, Lactobacillus* GG (*Lactobacillus rhamnosus* or *Lactobacillus casei* subspecies *rhamnosus*), *Lactobacillus gasseri, Lactobacillus johnsonii, Lactobacillus paracasei, Lactobacillus plantarum, Lactobacillus reuteri* and *Lactobacillus salivarus. Lactococcus* species include, without limitation, *Lactococcus lactis* and *Lactococcus plantarum. Bacillus* species include, without limitation, *Bacillus subtilis. Bifidobacterium* species include, without limitation, *Bifidobacterium adolescentis, Bifidobacterium bifidum, Bifidobacterium animalis, Bifidobacterium thermophilum, Bifidobacterium breve, Bifidobacterium longum, Bifidobacterium pseudolongum, Bifidobacterium infantis* and *Bifidobacterium lactis. Saccharomyces* species include, without limitation, *Saccharomyces boulardii* (*cerevisiae*).

In certain embodiments, the probiotic organisms include bacteria of the genus *Lactobacillus*, including *L. acidophilus* among many others known in the art, and of the genus *Bifidobacterium*, including *B. bifidum* (bifidus), *B. lactis*, and other *Bifidobacterium* species, and mixtures thereof.

More notably with regard to the present invention, the short-fatty acids produced by Bifidobacteria are a primary source of energy for colon epithelial cells. Therefore, Bifidobacteria have a direct synergistic support of the application of the present invention. Bifidobacteria consists of over 28 species, which are normal bacterial flora of the lower gastrointestinal tract. Bifidobacteria of the colon digest sugars to acidic short-chained fatty acids and slightly elevate the pH of gastrointestinal tract. Senna containing hydroxyanthracene glycosides that are not fully absorbed in the upper gastrointestinal tract are converted into pharmacologically active aglycones by microorganisms in the large intestine, which stimulates colonic motility and affects fluid and electrolyte balance in the colon. Thus, these probiotic microorganisms improve the function of plant-derived cathartic laxatives and their derivatives of claimed active cathartic significance formed before or after ingestion, e.g. the pharmacologically active aglycone derivatives. An effervescent plant-derived cathartic laxative system with an incorporated probiotic delivery system increases bioavailability and total clinically active compounds for laxative effect.

In certain embodiments, the plant-derived cathartic and the probiotic microorganism(s) are formulated together with the effervescence coupling system into a single composition, such as a tablet, granulated or powdered material. In such embodiments, the microorganisms can be incorporated into enteric coated matrices, delayed release systems, and/or microencapsulated or nanoencapsulated systems (see, e.g., Kailasapathy, K. 2002, Curr. Issues latest. Microbiol. 3: 39-48 for discussion of encapsulation). Upon dissolution of the dosage form in an aqueous medium, the effervescence is released to promote bioavailability of the plant-derived cathartic and the encapsulated microorganisms become suspended in the liquid for efficacious delivery to the gastrointestinal tract, thus achieving a jointly administered single cathartic laxative therapy for synergistic performance. As is appreciated in the art, encapsulation technology as applied to the probiotic microorganisms can be used to control release of the organisms in the gastrointestinal tract.

In other embodiments, the probiotic microorganisms are administered with the effervescent cathartic composition as a separate dosage unit (for example a tablet or capsule, which can employ micro- or nano-encapsulation technology) that is orally ingested in conjunction with the effervescent plant-derived cathartic drink. As described in greater detail below, the plant-derived cathartic and the probiotic can be packaged together in a kit, along with instructions for their administration. Modified and adapted cathartic compositions can be packaged together in a kit, long with instructions for their administration per rectum, as an alternative route of introduction into the gastrointestinal tract.

Similar to probiotic microorangisms, natural and synthetic enzymes introduced to a solid to liquid plant-derived cathartic formulation provide a distinct improvement to the action of anthraquinones, hydroxyanthracene glycosides, anthraglycosides, and their cathartically active derivatives. Thus, in another embodiment, the effervescent cathartic composition is administered together with natural or synthetic enzymes that achieve, in vitro and in vivo, the same ends as the probiotic microorganisms generally achieve in vivo, either instead of or in conjunction with the microorganisms. Some examples of enzymes that break down nutrients and/or convert prodrugs to active drugs, include but are not limited to: amylase, protease, lipase, trypsin, papain, bromelain, lysozyme, chymotrypsin, esterases, carboxylesterases, acetylcholinesterase, butyrylcholinesterase, paraoxonase, and arylesterase, pancreatic enzymes, and liver enzymes. This embodiment can also utilize (1) enteric coated matrices, delayed release systems, and/or microencapsulated or nanoencapsulated systems to incorporate the enzymes into the effervescent plant cathartic laxative formulation to form a jointly administered single cathartic laxative therapy for synergistic performance; or (2) formulation of the probiotic microorganisms and/or enzyme as a separate oral dosage unit.

In one embodiment, amylase is administered in conjunction with the effervescent plant-derived cathartic. Amylase breaks down starch (complex carbohydrates) into dextrins and sugars. The plant-derived cathartics of the invention are carbohydrates and sugar derivatives (i.e. glycosides and the like) that would benefit from the catalytic action of this enzyme. Thus, microorganisms, as mentioned herein, and enzymes, such as amylase, contribute to the novel effectiveness of an effervescent plant cathartic laxative formulation and system. Enzymes, all or a portion, can further be microencapsulated with enteric coated properties to bypass the acidic environment of the stomach and reach other segments of the lower gastrointestinal tract to facilitate the plant-derived cathartic laxative mechanism in vivo, while un-coated or non-microencapsulated enzyme product may work catalytically after the composition is dissolved into the aqueous medium, prior to user administration.

In certain embodiments, the composition comprises a combination of probiotic microorganisms and enzymes.

The composition described above, comprising a plant-derived cathartic and an effervescence coupling system, offers numerous advantages over currently available cathartic compositions. Some of those advantages arise from the effervescence generated upon dissolution of the solid dosage form into an aqueous medium. Other benefits arise directly from the fact that the solid dosage form dissolves readily and conveniently into an aqueous medium, such as water, which is a distinct improvement over currently available cathartic dosage forms. Furthermore, as described above, the liquid volume can accelerate interaction among system components, and such liquid volumes can reach more clinically relevant surface areas of the gastrointestinal tract or otherwise.

Accordingly, another aspect of the invention features a solid composition comprising one or more plant-derived cathartics, formulated to dissolve or disperse in an aqueous medium to form a liquid composition, which is then consumed or administered. In certain embodiments, the solid dosage form dissolves readily into an aqueous medium, such as water, at room temperature. In one embodiment, the dosage form dissolves or disperses in an aqueous medium within a few minutes, e.g., 10-15 minutes of contact with the medium. In another embodiment, the dosage form dissolves or disperses in an aqueous medium in less than 10 minutes, e.g., 9, 8, 7, 6, or 5 minutes, or in other embodiments, within 4, 3, 2 or 1 minute of contact with the medium. The dissolution or dispersion can be accomplished with our without gentle stirring or agitation.

These solid dosage forms are formulated at the dosages described above for the effervescence-generating compositions. They may comprise at least one probiotic microorganism, at least one enzyme, or a combination thereof; as well as all the other additional ingredients and the like described above for the effervescence-generating compositions.

Another aspect of the present invention features a method of administering a plant-derived cathartic to an individual. The method comprises (1) formulating the plant-derived cathartic together with an effervescence coupling system into a dosage form (e.g., tablet, granules or powder), as described above, (2) dissolving the a dosage unit into an aqueous medium, thereby producing an effervescent liquid comprising the plant-derived cathartic, and (3) administering the liquid to the individual. Typically, the liquid is taken by mouth. However, in certain circumstances it may be administered via gastric tube or inserted rectally.

The method may be performed for one or more purposes, including but not limited to: loosening stools, softening stools, cathartic bowel evacuation, treatment of constipation, treatment of bowel impaction, and as a purgative for dieters' weight loss.

Any of the cathartic liquid compositions described above can be ingested as soon as the solid dosage form has dissolved. However, as noted herein, certain advantages can be obtained by delaying consumption by minutes or even hours after the solid has dissolved. This is because the increased exposure of the plant-derived cathartic to the liquid volume and/or the effervescence facilitates chemical and physical reactions that increase the amount and availability of the active components. Thus, in one embodiment, an individual may wait a few minutes, e.g., 1, 2, 3, 4, 5, 6, 7, 8, 9 or 10 minutes, or several minutes, e.g., 15, 20, 25, 30, 35, 40, 45, 50 or 55 minutes, or a few hours, e.g., 1, 1.5, 2, 2.5, 3, 3.5, 4, 4.5, 5, 5.5, 6, 6.5, 7, 7.5 or 8 hours or more before consuming the liquid. It has been observed that some individuals sip the cathartic drink over many hours throughout the course of a day to control or modulate the laxative effect intensity that individually suits their needs and comfort level based on their own body's feedback mechanisms. Furthermore, the common use of using standard commercially available "bottled drinking water" for product dissolution further aids consumer therapy compliance, convenience, and ability to modulate the laxative intensity by the conveniently preparing the novel cathartic drink formulation at will by the consumer who may (1) immediately drink the product or (2) sip it over an extended duration of hours. Thus, in one embodiment, the solid dosage unit can be dissolved in the liquid, e.g., in the morning and consumed in the evening. In another embodiment, the solid dosage unit can be dissolved in the liquid, e.g., in the morning and consumed throughout the day. In a convenient embodiment, the solid dosage unit can be dissolved in a prepared beverage, such as bottled water, which can be easily carried and consumed throughout the day.

In one embodiment, the cathartic composition contains plant-derived cathartics as active ingredients. These include plant products extracts, compounds, or combinations thereof, as described thereof. In other embodiments, the effervescent cathartic composition further comprises probiotic microorganisms as described above. In still other embodiments, the cathartic composition further comprises beneficial enzymes as described above. In yet other embodiments, the cathartic composition further comprises combinations of probiotics and beneficial enzymes as described thereof.

The cathartic compositions of the invention can be administered alone or in conjunction with other agents (e.g., probiotics and/or beneficial enzymes) to promote digestion or elimination, or to augment the effect of the plant-derived cathartic as described above. One way to administer the cathartic composition in conjunction with the other agents is to formulate them together into the same dosage form. Alternatively, the other agents can be formulated into separate dosage forms as described above, and administered in conjunction with the cathartic composition of the invention. In these embodiments, the separate dosage forms can be administered, e.g., at the same or different time, and/or the same or different frequency, using the same or different administration routes. The additional agents can be given about the same time or periodically. "About the same time" generally means that the substances are administered at the same time or within about 72 hours of each other. "Periodically" means that the substance is administered on a dosage schedule acceptable for a specific substance.

Another aspect of the present invention features kits suitable for use in administering a plant-derived cathartic to an individual. The kits comprise in separate containers in a single package or in separate containers in a virtual package, as appropriate for the kit component: (a) one or more plant-derived cathartic-containing solid dosage form that, upon dissolution in an aqueous medium, produces a liquid, optionally effervescent cathartic composition; and (b) instructions for how to use the kit components for the benefit of an individual. The kits optionally comprise additional agents for promoting laxation, enhancing the effectiveness of the cathartic composition, or other gastrointestinal benefit. Suitable additional agents for inclusion in the kits include, but are not limited to: (1) one or more probiotic microorganisms formulated into beneficial dosage forms as described above, to promote digestion or gastrointestinal health and/or enhance the effectiveness of the effervescent cathartic composition; and (2) one or more enzymes as described above, which promote digestion or gastrointestinal health and/or enhance the effectiveness of the cathartic composition.

In another of its several aspects, the invention provides packages comprising a plant-derived cathartic-containing solid dosage form that, upon dissolution in an aqueous medium, produces a liquid, optionally effervescent, cathartic composition and a label affixed to the package containing a word or words, picture, design, symbol, acronym, slogan, phrase, or other device, or combination thereof, that indicates that the contents of the package contains a composition suitable for promoting laxation in an individual. In certain embodiments, the solid dosage form is packed in hermetically sealed moisture proof sachets, foils, or blister packs.

Another aspect of the invention features devices, methods and/or articles of manufacture for communicating information about or instructions for use of the cathartic composition and/or other beneficial agents, or kits/packages comprising one or more such agents, as described herein. Typically, such devices and the like comprise one or more of a physical or electronic document, digital storage media, optical storage media, audio presentation, audiovisual display, or visual display containing the information or instructions.

The device, method or article of manufacture can be a displayed website, a visual display kiosk, a brochure, a product label, a package insert, an advertisement, a handout, a public announcement, an audiotape, a videotape, a DVD, a CD-ROM, a computer-readable chip, a computer-readable card, a computer-readable disk, a USB device, a FireWire device, a computer memory, or any combination thereof.

Another aspect of the invention features methods of manufacturing the solid dosage forms comprising plant-derived cathartics. The methods typically comprise combining active and inactive ingredients and forming them into the desired solid dosage form convenient for dissolution into an aqueous medium to produce the liquid dosage form. In one embodiment, an effervescence coupling system is included and the resulting liquid dosage form is effervescent. For example, two titrations of respective ingredients (one acid and one base) are prepared. Active and inactive ingredients are mixed to into one titration element or the other based on suitable chemical stability. Each titration is homogenously mixed into a paste employing such solvents as ethanol, acetone, and water. The paste is dried into a granulation of various particle sizes. The resultant granulation can be screened into a gradient of desires particle sizes for each titration, respectively. Then the two screened granulation sets are homogenously combined together. In one embodiment, they are combined employing a binder, such as fructose, and a lubricant, such as magnesium stearate, and this mixture is pressed into a tablet.

Alternatively, this final mixture may be left as a free flowing granular or powder dosage form for consumption as a convenient ready mix drink for dissolution in any aqueous liquid.

The following examples are provided to describe the invention in greater detail. They are intended to illustrate, not to limit, the invention.

Example 1

An effervescent senna tablet containing a percentage of active plant-derived laxative ingredient comparable to an OTC tablet of 8.6 mg of sennosides was prepared. The manufacture of such an effervescent tablet is known to those skilled in the art of effervescent manufacturing, and employs a pharmaceutically suitable effervescence coupling system. The formula composition is as follows:

| | |
|---|---|
| Senna Extract (10% sennosides*) | 3.4% |
| Citric Acid | 41.7% |
| Sodium Bicarbonate | 44.3% |
| Fructose | 3.2% |
| Flavor | 6.1% |
| Stevia | 0.5% |
| Riboflavin | 0.09% |
| Magnesium Stearate | 0.4% |

*Note:
Senna Extract standardized 10% sennosides used above. Depending on mass and volume restrictions, Senna Extract Standardized 20% sennosides may be substitutable with half the measured mass of extract required.

Example 2

An effervescent senna tablet containing a percentage of active plant-derived laxative ingredient comparable to that which delivers approximately half the sennosides (75 mg) of a "Cali Girl Brand Dieter's Drink" (a steeped senna leaf tea drink) is listed below.

| | |
|---|---|
| Senna Extract (10% sennosides) | 30.1% |
| Citric Acid | 26.5% |
| Sodium Bicarbonate | 28.1% |
| Fructose | 2% |
| Flavor | 12% |
| Stevia | 0.7% |
| Magnesium Stearate | 0.4% |

Example 3

Another effervescent senna tablet containing a percentage of active plant-derived laxative ingredient comparable to that which delivers approximately 100% of the sennosides (150 mg) of a "Cali Girl Brand Dieter's Drink" (a steeped senna leaf tea drink) is listed below.

| | |
|---|---|
| Senna Extract (20% sennosides) | 30.1% |
| Citric Acid | 26.5% |
| Sodium Bicarbonate | 28.1% |
| Fructose | 2% |
| Flavor | 12% |
| Stevia | 0.7% |
| Magnesium Stearate | 0.4% |

Example 4

An effervescent tablet containing a percentage of two active plant-derived laxative ingredients, Senna Extract and Cascara Sagrada Extract, employs two parts Senna Extract to one part Cascara Sagrada. The formula composition is as follows:

| | |
|---|---|
| Senna Extract | 20% |
| Cascara Sagrada Extract | 10% |
| Citric Acid | 26.5% |
| Sodium Bicarbonate | 28.1% |
| Fructose | 2% |
| Flavor | 12% |
| Stevia | 0.7% |
| Magnesium Stearate | 0.4% |

Example 5

A modified version of the preparation of Example 4 employs incorporating into the composition of the effervescent tablet microencapsulated live Bifidobacteria for colloidal suspension post in vitro effervescent tablet dissolution into an aqueous liquid for oral ingestion.

| | |
|---|---|
| Microencapsulated Bifidobacteria | 5% |
| Senna Extract | 15% |
| Cascara Sagrada Extract | 10% |
| Citric Acid | 26.5% |
| Sodium Bicarbonate | 28.1% |
| Fructose | 2% |
| Flavor | 12% |
| Stevia | 0.7% |
| Magnesium Stearate | 0.4% |

Example 6

Another modification of Examples 4 and 5 employs the concomitant consumption a separate oral dosage capsule containing live Bifidobacteria, which is ingested concurrently with the post in vitro dissolved effervescent tablet liquid drink.

Administration: both Component A and Component B are for concurrent oral ingestion.

Component A:

| | |
|---|---|
| Senna Extract | 20% |
| Cascara Sagrada Extract | 10% |
| Citric Acid | 26.5% |
| Sodium Bicarbonate | 28.1% |
| Fructose | 2% |
| Flavor | 12% |
| Stevia | 0.7% |
| Magnesium Stearate | 0.4% |

Component B:
An oral dosage capsule containing Microencapsulated *Bifidobacteria* $10^9$ live

Example 7

A modification of Example 5, which employs the incorporation of microencapsulated live Bifidobacteria for colloidal suspension post in vitro effervescent tablet dissolution into an aqueous liquid for oral ingestion, the senna extract and Cascara Sagrada extract are substituted with sennosides and sasanthranols, respectively. Furthermore, sasanthranols may also be substituted with cascarosides, and their mixtures thereof, and microencapsulated Bifidobacteria may also be substituted with a facilitating enzyme(s), and their mixtures thereof. Microorganisms and enzymes activate naturally occurring plant-derived cathartic prodrug compounds into more biologically active cathartic laxative derivatives. Microencapsulated amylase is a useful enzyme to substitute for microencapsulated Bifidobacteria or include as a mixture thereof.

| Microencapsulated Bifidobacteria (/enzymes) | 5% |
|---|---|
| Sennosides | 2% |
| Casanthranols (/Cascarosides) | 1% |
| Citric Acid | 37.3% |
| Sodium Bicarbonate | 39.7% |
| Fructose | 2% |
| Flavor | 12% |
| Stevia | 0.7% |
| Magnesium Stearate | 0.4% |

Example 8

A modification of Example 4, which employs a method to enhance the formula composition of the effervescent tablet's clinical performance with the concomitant consumption a separate oral dosage capsule containing live Bifidobacteria that is ingested concurrently with the post in vitro dissolved effervescent tablet liquid drink, has the senna extract and the Cascara Sagrada extract substituted with sennosides and casanthranols, respectively. Furthermore, casanthranols may also be substituted with cascarosides, and their mixtures thereof, and microencapsulated Bifidobacteria may also be substituted with a facilitating enzyme(s), and their mixtures. Microorganisms and enzymes activate naturally occurring plant-derived cathartic prodrug compounds into more biologically active cathartic laxative derivatives. Microencapsulated amylase is a useful enzyme to substitute for microencapsulated Bifidobacteria or include as a mixture thereof in Component B.

Administration: both Component A and Component B are for concurrent oral ingestion.

Component A:

| Sennosides | 2% |
|---|---|
| Casanthranols (/Cascarosides) | 1% |
| Citric Acid | 39.8% |
| Sodium Bicarbonate | 42.2% |
| Fructose | 2% |
| Flavor | 12% |
| Stevia | 0.7% |
| Magnesium Stearate | 0.4% |

Component B:
An oral dosage capsule containing Microencapsulated Bifidobacteria $10^9$ live cells or equivalent enzymes.

Example 9

Five tablets prepared as set forth in Example 1 were placed in 240 ml of water at room temperature of 75° F., and the amount of time to complete dissolution and stoppage of fizzing and all solids dissolved was measured. The average time for all timed trials was 3 minutes and 54 seconds. Similarly, the procedure was repeated using 180 ml of water and similar results were obtained. In addition, it was also discovered that gentle stirring with could reduce the dissolving time by about 30 seconds.

Example 10

Multiple flavors were tested individually and in various combinations. The most desirable flavors were apple, sour apple, raspberry, and watermelon. Using a proprietary blend of these flavors created a desirable taste, color, and appearance in the invention.

Four individuals took each one flavored effervescent tablet of the formulation described in Example 1. All four individuals described the product as visually acceptable and having a very good taste. All four individuals indicated rapid clinical effectiveness after use as well.

Example 11

A comparative study for the expected total sennosides of effervescent tablet from Example 1 was conducted to analyze and compare findings against two standardized supply stocks of Senna Extract. One supplier provided standardized stock sample of Senna extract claimed to contained 20% w/w sennosides, and another supplier provided a standardized stock sample of Senna extract claimed to contain 10% w/w sennosides. The effervescent tablet from Example 1 was made using the standardized stock sample of Senna extract claimed to contain 10% w/w sennosides.

Senna extract were claimed to contained 20% w/w and 10% w/w sennosides and the tablets of the invention from Example 1 were sent to an independent analytical laboratory to determine the total sennosides present in each of the three samples using high pressure liquid chromatography (HPLC). All three sample underwent the same analytical assay protocol with the exception that the tablet of the invention could dissolve itself into solution for laboratory testing. The results are shown in the table below:

| Sample | Claimed | Obtained Yield | % Deviation |
|---|---|---|---|
| Standard Stock 20% | 200 mg | 163.6 mg | 18.2% lower |
| Standard Stock 10% | 100 mg | 55.3 mg | 44.7% lower |
| Example 1 Tablet | 8.6 mg | 8.9 mg | +3% higher |

It is evident from the above data that the tablet of the invention unexpectedly provided surprisingly higher dissolution in vitro for total sennosides than either of the stock senna extracts the 20% w/w or the 10% w/w. Note that the tablet of the invention from Example 1 was created from the same stock extract of standardized 10% w/w sennosides. The deduced conclusion indicates a positive intrinsic effect of the effervescent mechanism on the senna extract and constituent sennosides increased dissolution rate and solubility profile.

The same independent laboratory that from Example 10 also carried out a separate degradation study to ensure that users of the effervescent plant cathartic laxative formulation would perform and not undergo any significant degradation of the active plant cathartic, i.e. sennosides—after going through an effervescent acid—base reaction and if the resultant solution was left standing by the user for any extended time. Results are presented below.

| Analyses | Claimed | Method | Result |
|---|---|---|---|
| t-0 Degradation Test*: Total Sennosides | 8.6 mg | HPLC | 8.07 mg/tablet |
| t-30 minutes: Total Sennosides | NA | HPLC | 8.29 mg/tablet |
| t-60 minutes: Total Sennosides | NA | HPLC | 8.42 mg/tablet |
| t-90 minutes: Total Sennosides | NA | HPLC | 8.34 mg/tablet |

*Degradation Test: Dissolved two effervescent tablets in 180 ml of room temperature water.

Timing and sampling after complete dissolution with continuous slow stirring.

The results demonstrate that there was no decrease or degradation of the active sennosides over time. Indeed, it appears that more sennosides were dissolved into solution over time. It may be assume that a user of the effervescent drink would consume it within 15 minutes from reconstitution with water. However, these results suggest that active sennosides increase over time, so benefit is obtained by increasing the time between initial dissolution of the dosage and consumption of the drink.

The present invention is not limited to the embodiments described and exemplified above, but is capable of variation and modification within the scope of the appended claims.

What is claimed:

1. A composition that promotes emptying of the bowels, comprising therapeutically effective amounts of *Cassia senna* and *Bifidobacterium* and an effervescence coupling system, wherein the composition is in a form selected from the group consisting of tablet, powder and capsule.

2. The composition of claim 1, further comprising one or more additional plant-derived cathartics from plants selected from the group consisting of: canafistula (*Cassia fistula*); common buckthorn (*Rhamnus cathartica*), alder buckthorn (*Rhamnus frangula*), cascara buckthorn (*Rhamnus persiana*); fo-ti (*Polygonum multiflorum*); and damiana (*Turnera diffusa*).

3. The composition of claim 1, wherein the effervescence coupling system comprises an acid-base coupling system.

4. The composition of claim 3, wherein the base comprises a carbonate or bicarbonate and the acid is citric acid, fumaric acid, adipic acid, malic acid, tartaric acid, salts thereof or combinations thereof.

5. The composition of claim 1, wherein the tablet, powder or capsule dissolves or disperses in an aqueous medium to form a liquid composition prior to administration to an individual.

6. The composition of claim 1, further comprising one or more additional ingredients selected from probiotic microorganisms, enzymes, stool softeners, osmotic laxatives, magnesium hydroxide; soluble and insoluble dietary fiber, antiflatulents, antibloating agents, nutraceuticals, B vitamins, brewers yeast, and combinations thereof.

7. The composition of claim 6, wherein the other probiotic microorganisms are of genera selected from *Bacillus, Enterococcus, Lactobacillus, Lactococcus, Saccharomyces, Streptococcus*, and combinations thereof.

8. The composition of claim 6, wherein the enzymes are selected from amylase, protease, lipase, trypsin, papain, bromelain, lysozyme, chymotrypsin, esterases, carboxylesterases, acetylcholinesterase, butyrylcholinesterase, paraoxonase, and arylesterase, pancreatic enzymes, liver enzymes, and combinations thereof.

* * * * *